(12) United States Patent
Kato et al.

(10) Patent No.: US 9,033,649 B2
(45) Date of Patent: May 19, 2015

(54) CORROSIVE ENVIRONMENT MONITORING SYSTEM AND CORROSIVE ENVIRONMENT MONITORING METHOD

(75) Inventors: Hideo Kato, Kanagawa (JP); Yoshihiro Sakai, Kanagawa (JP); Kenji Nakamura, Kanagawa (JP); Mitsuo Yamashita, Kanagawa (JP)

(73) Assignee: Fuji Electric Co., Ltd., Kawasaki-shi, Kanagawa (JP)

( * ) Notice: Subject to any disclaimer, the term of this patent is extended or adjusted under 35 U.S.C. 154(b) by 548 days.

(21) Appl. No.: 13/388,088

(22) PCT Filed: Jul. 29, 2010

(86) PCT No.: PCT/JP2010/004804
§ 371 (c)(1),
(2), (4) Date: Jan. 31, 2012

(87) PCT Pub. No.: WO2011/021351
PCT Pub. Date: Feb. 24, 2011

(65) Prior Publication Data
US 2012/0128469 A1 May 24, 2012

(30) Foreign Application Priority Data
Aug. 17, 2009 (JP) ................................. 2009-188333

(51) Int. Cl.
*G01N 17/02* (2006.01)

(52) U.S. Cl.
CPC ....................................... *G01N 17/02* (2013.01)

(58) Field of Classification Search
CPC .................................. F01D 5/14; G01N 17/02
USPC ............ 415/118, 169.1–169.4; 416/1, 35, 61, 416/230, 241 R; 137/590, 592
See application file for complete search history.

(56) References Cited

U.S. PATENT DOCUMENTS

| | | | | |
|---|---|---|---|---|
| 3,595,774 A | * | 7/1971 | Bremerman | 204/196.36 |
| 3,633,099 A | * | 1/1972 | Richman | 324/71.1 |
| 4,283,200 A | * | 8/1981 | Bodmer et al. | 436/6 |

(Continued)

FOREIGN PATENT DOCUMENTS

| | | |
|---|---|---|
| JP | 08-074075 A | 3/1996 |
| JP | 09-170704 A | 6/1997 |

(Continued)

OTHER PUBLICATIONS

English Translation of the International Preliminary Report on Patentability (Chapter II) dated Feb. 23, 2012 for PCT/JP/2010/004804.

(Continued)

*Primary Examiner* — Dwayne J White
*Assistant Examiner* — Brian P Wolcott
(74) *Attorney, Agent, or Firm* — Young Basile Hanlon & MacFarlane P.C.

(57) ABSTRACT

Provided are corrosive environment monitoring systems and methods whereby corrosive factors are measured in a steam turbine and a corrosive environment is correctly monitored. A corrosive environment monitoring system measures corrosive factors having a part in damaging and deteriorating structural members in a steam turbine and is configured in such a way that steam in the steam turbine is permitted to flow into the corrosive environment monitoring system. Furthermore, in the steam turbine, a condensing mechanism condenses steam that has flowed in and a corrosive factor measuring device is equipped with corrosive factor sensors that measure corrosive factors in condensed water generated by the condensing mechanism.

16 Claims, 5 Drawing Sheets

(56) References Cited

U.S. PATENT DOCUMENTS

| | | | |
|---|---|---|---|
| 4,386,498 A * | 6/1983 | Lee et al. | 60/646 |
| 4,488,939 A * | 12/1984 | Fu | 205/777 |
| 4,840,719 A * | 6/1989 | Jasinski | 204/404 |
| 5,188,715 A * | 2/1993 | Chen et al. | 205/776 |
| 5,984,628 A * | 11/1999 | Gray et al. | 415/169.4 |
| 6,628,111 B2 * | 9/2003 | Shapiro et al. | 324/71.2 |
| 7,141,859 B2 * | 11/2006 | DeBoer et al. | 257/414 |
| 7,152,624 B2 * | 12/2006 | Frederiksen | 137/554 |
| 2007/0120572 A1 | 5/2007 | Chen et al. | |
| 2011/0027063 A1 * | 2/2011 | Hefner et al. | 415/1 |

FOREIGN PATENT DOCUMENTS

| | | |
|---|---|---|
| JP | 2001-041860 A | 2/2001 |
| JP | 2001-116715 A | 4/2001 |
| JP | 2002-131261 A | 5/2002 |
| JP | 2004-003403 A | 1/2004 |
| JP | 2009-144952 A | 7/2009 |
| TW | 200728704 A | 8/2007 |

OTHER PUBLICATIONS

Office Action issued by the Taiwan Patent Office for the corresponding Taiwan Patent Application No. 099126754 dated Sep. 9, 2014 and an English translation thereof.

Office Action issued by the Icelandic Patent Office for the corresponding Icelandic Patent Application No. 050028 dated Oct. 28, 2014.

* cited by examiner

CORROSIVE ENVIRONMENT MONITORING SYSTEM AND CORROSIVE ENVIRONMENT MONITORING METHOD

TECHNICAL FIELD

The present invention relates to a corrosive environment monitoring system and a corrosive environment monitoring method for measuring corrosive factors participating in damage and degradation of a structural member provided inside of a steam turbine.

BACKGROUND

In a steam turbine, material degradation due to high-temperature heat degradation of a member caused by operating temperature, creep and thermal fatigue degradation, and material degradation resulting from corrosion damage to constructional members of the turbine caused by steam quality have become critical factors governing the life of the steam turbine.

For the former case, it springs from material degradation of the member per se, and therefore it can non-destructively inspect and measure changes in hardness and precipitates of member materials, for understanding of the changes, during routine inspection, and compare the inspected and measured results with a previously acquired deterioration base curve of measurement parameters, thus estimating the residual life of the member.

For the latter case where corrosion is taking part in the material degradation, however, it tends to be become more complex, because of convolution of various factors, differing from relatively stable factors suited for a turbine operation as in the former case, such as temperature, stress, and time. More precisely, the various factors include a change in steam water quality in operation, corrosion resistance of each member, and a difference in environmental conditions varying every vapor flows, temperature distribution in the turbine, surfaces to be exposed to steam, a clearance gap, a degree of condensation in suspension, and a contact part of dissimilar materials. Frequency in operation and suspension, frequency in condensation, and frequency in turbine opening are also important factors. Particularly where a turbine works using geothermal steam, the turbine suffers from large water quality variations, every field of respective plants, and comes to be further added an effect factor to materials by hydrogen sulfide. Corrosion damage due to steam water quality to a member installed in the turbine is a dominant factor governing the life of the geothermal steam turbine.

As a device for detecting such steam water quality, there has been conventionally proposed a steam purity monitoring system, comprising a steam drain device for cooling geothermal steam, and for condensing and liquefying water vapor contained in the geothermal steam; an anion exchange resin for carrying out anion exchange reaction with ingredients contained in the liquefied steam drain; and an electric conductivity measuring means for measuring electric conductivity of the steam drain after the anion exchange reaction, wherein the electric conductivity is measured and monitored as an index indicative of ingredients of the dissolved solids contained in the geothermal steam (e.g. see JP 2002-131261 A).

Also, there has been proposed a corrosive environment damage diagnosis method of mechanical structural parts and a device therefore, comprising detecting and monitoring, at all times, accelerated corrosion parameters of mechanical structural parts materials placed in a corrosive environment, and a corrosive resistance parameter of mechanical structural parts materials; determining whether the corrosive environment inflict damage on the mechanical structural parts materials based on the detected results of the corrosion accelerated parameters; calculating corrosion damage resistance properties based on the detected results of the corrosion resistance parameters; and diagnosing the mechanical structural parts by successively calculating the progress of corrosion damage based on the corrosion damage resistance properties, with a period of time limited to that during which the corrosive environment inflicts corrosive damage on the mechanical structural parts materials, whereby quantitatively treats corrosive environment damage diagnosis of the mechanical structural parts (see e.g. JP 2001-41860 A).

Further, there has been proposed a water quality monitor for vapor condensed water and an energy conversion system used thereof, comprising producing condensed water by a condensing chamber provided for simulation of condensation conditions in the vicinity of a surface of a steam turbine blade; monitoring water quality by analyzing the condensed water; and measuring pH, electric conductivity, ingredient and concentration of chemical species, corrosion potential, and the total organic carbon concentration; and performing control operating conditions of the steam turbine and injection of chemicals based on the measured results (e.g. see JP 09-170704 A).

Furthermore, there has been proposed a steam turbine system equipped with a condensed water storage to temporarily store condensed water discharged from a low-pressure turbine, for the purpose of previously and effectively preventing corrosion damage to turbine structural materials by injecting anti-corrosive chemicals as much as a proper quantity fit for corrosion patterns, wherein the system is arranged to immerse a sample electrode made of materials with the same ingredients as constructional materials of the low-pressure turbine and a reference electrode serving as a reference of potential into the condensed water in the condensed water storage; measure a potential difference between the reference electrode and the sample electrode by a chemical injection control device; and calculate types and injection volume of injection chemicals so that the measured potential difference falls within a potential range set by measuring pH of the condensed water and chloride ion concentration of the structural materials of the low-pressure turbine (e.g. see JP 08-74075 A).

SUMMARY

In JP 2002-131261 A, the system has really exercised ingenuity, to some extent, to supply the geothermal steam to be supplied to the steam turbine to the steam drain device for cooling; condense and liquefy vapor contained in the geothermal steam; carry out anion exchange reaction with ingredients in the liquefied steam drain utilizing an anion exchange resin; measure the electric conductivity of the steam drain after the anion exchange reaction; and measure thereby the ingredients of the dissolved solids contained in the geothermal steam. However, the system is not devised disappointingly for employing the condensed water in an actual steam turbine, and so leaves a problem unresolved that the system fails to do accurate monitoring of corrosive environment at a blade of the steam turbine.

Further, in JP 2001-41860, the system has really exercised ingenuity, to some extent, to arrange a sensor of a corrosive environment monitoring sensor to casing of a low-pressure turbine; and to arrange a sample electrode made of the same materials as those of a steam turbine low-pressure section or a gas turbine compressor, of electrochemically equal thereto, or of similar thereto, a pair of platinum electrode, and a reference electrode, at a position of an inner surface of the casing of the sensor, thereby measuring the accelerated corrosion parameters in the presence of small water droplets (condensed water) at a tip of the pair of the platinum electrode pair, and measuring the accelerated resistance parameter (condensed water) in the presences of small water droplets between the sample electrode and the reference electrodes. However, the system leaves a problem unresolved that the system fails to directly measure pH or chloride ion concentration, etc., that constitutes a corrosion factor of the condensed water.

Furthermore, in JP 09-170704 A, the system has really exercised ingenuity, to some extent, to produce the condensed water by the condensing chamber which is provided for simulation of the condensation conditions in the vicinity of the surface of the steam turbine blade, and measure the water quality of the condensed water by means of a pH sensor, a reference electrode, a dissolution oxygen sensor, a thermometer, an ion sensor, a metal electrode, an electric conductivity meter, and a counter electrode, etc. However, they are not devised disappointingly for analyzing the condensed water in the vicinity of the surface of the actual steam turbine blade, and so leave a problem unresolved that the system fails to provide accurate results of the analysis in the vicinity of the surface of the actual steam turbine blade.

Moreover, in JP 08-74075 A, the system has really exercised ingenuity, to some extent, to temporarily store in the condensed water storage the condensed water discharged from the low-pressure turbine, and detect pH and chloride ion concentration by immersing a pH meter and an ion densitometer into the stored condensed water. Even in this case, they are not devised disappointingly for detecting pH and chloride ion concentration in the low-pressure turbine, and so leave a problem unresolved that the system fails to do accurate corrosive environment monitoring.

The present invention is made aiming at the problems of the prior art awaiting solution and its objective is to provide a corrosive environment monitoring system and a corrosive environment monitoring method capable of measuring corrosion factors inside of the steam turbine to provide accurate corrosive environment monitoring.

To accomplish the above-indicated objective, in a corrosive environment monitoring system for measuring a corrosion factor participating in damage degradation of a structural member inside of a steam turbine according to one embodiment, a corrosion factor measuring device is provided inside of the steam turbine equipped with a condensing chamber for condensing flowed in steam, which has a structure allowing for influx of steam within the steam turbine thereinto, and is provided with a condensed water storage configured to be capable of storing the condensed water produced by condensing the flowed in steam and have a structure imitating a clearance gap inside of the steam turbine, as well as with a corrosion factor sensor for measuring the corrosion factor of the condensed water inside of the condensed water storage.

The corrosion environment monitoring system according to yet another embodiment includes a temperature control section having a cooling function of condensing the steam flowed into the condensing chamber.

The corrosion environment monitoring system according to yet another embodiment includes the corrosion factor measuring device being composed of at least three types of sensors consisting of a corrosion potential sensor, a pH sensor, and a chloride ion sensor.

The corrosion environment monitoring system according to still another embodiment includes the corrosion potential sensor being a sample member electrode made of the same material as the structural member and a reference electrode, the sample member electrode and the reference electrode being immersed into condensed water stored in the condensed water storage.

The corrosion environment monitoring system according to yet another embodiment includes an electric conductivity sensor in addition to the three types of sensors.

The corrosion environment monitoring system according to yet another embodiment includes a carbon dioxide gas sensor and a hydrogen sulfide sensor in addition to the three types of sensors.

The corrosion environment monitoring system according to yet another embodiment includes that the condensed water storage is configured to have a structure for simulating a fitting clearance formed between a moving blade and a turbine rotor inside of the steam turbine.

The corrosion environment monitoring system according to yet another embodiment includes that the steam turbine is composed of a high-pressure turbine, a middle-pressure turbine, and a low-pressure turbine, and the corrosion factor measuring device is arranged at a position where a part of steam flux flowing inside of a turbine blade cascade can be sampled, without affecting the steam flux inside of the turbine blade cascade, in a casing of the low-pressure turbine.

The corrosion environment monitoring system according to yet another embodiment further comprises a corrosion factor analyzer for conducting evaluation and judgment processing of the corrosion factor, the corrosion factor analyzer including a corrosive environment state factor determining device which compares corrosion factor measured data measured by the corrosion factor measuring device and a control reference range of a corresponding corrosion factor, and raises an alarm when the corrosion factor measured data goes beyond the control reference range.

The corrosion environment monitoring system according to still another embodiment further comprises a corrosion factor analyzer for conducting evaluation and judgment processing of the corrosion factor, the corrosion factor analyzer including the residual life diagnosis device which predicts the progress of corrosion damage to the structural member based on a previously prepared correlation with influence on the corrosion damage of the structural member, and finds the residual life of the structural member, on the basis of the corrosion factor measured data measured by the corrosion factor measuring device.

A corrosion environment monitoring method of measuring a corrosion factor participating in damage degradation of a structural member inside of a steam turbine according to one embodiment of the present invention comprises producing condensed water by flowing steam standing in the steam turbine for condensation into a condensing chamber provided in the steam turbine when the steam turbine is in operation; conducting at all times corrosion factor measurement which a corrosion factor is measured during operation of the steam turbine by contacting a corrosion factor sensor with the produced condensed water; analyzing the corrosion factor of the condensed water by gathering the condensed water in a structural member inside of the steam turbine when the steam turbine is not in operation; comparing corrosion factor measured data when the steam turbine is in operation and corrosion factor analyzed data when the steam turbine is not in operation; and finding a correlation between them to adopt it as a management indication.

Further, the corrosion environment monitoring system according to yet another embodiment further comprises a corrosion factor analyzer for conducting evaluation and judgment processing of the corrosion factor, the condensed water in the structural member inside of the steam turbine being gathered when the steam turbine is not in operation to supply data obtained by detecting the corrosion factor of the condensed water to the corrosion factor analyzer, and a correlation being found between a corrosion factor measured value when the steam turbine is in operation and a corrosion factor measured value when the steam turbine is not in operation to adopt it as a management indicator.

Furthermore, in the corrosion environment monitoring system according to still another embodiment, the condensed water storage has an orifice provided at a low pressure side.

Moreover, in the corrosion environment monitoring system according to still yet another embodiment, the condensed water storage has one end communicating with a communication hole formed on an inner peripheral wall of the casing, and has the other end communicating with a low pressure side inside of the casing through the orifice.

Besides, in the corrosion environment monitoring system according to still another embodiment, a conduit is provided in the steam turbine, which extends from an outer casing at an outermost periphery up to the condensed water storage passing through an inner casing, the corrosion factor sensor is inserted into the conduit to dip a lower end of the corrosion factor sensor into the condensed water stored in the condensed water storage, and the conduit is movably mounted between a condensed water blocking position where the underside of the conduit comes into contact with the base of the condensed water storage and a condensed water passing position where the underside of the conduit is substantially flush with an upper surface of the condensed water storage.

Since the present invention takes the line of providing the condensing mechanism for condensing steam in the steam turbine, and measuring corrosion factors of the condensed water produced by the condensing mechanism, the present invention may offer direct monitoring of the corrosion factors in the steam turbine in operation, which provides an advantageous effect of allowing accurate corrosive environment monitoring.

BRIEF DESCRIPTION OF THE DRAWINGS

The various features, advantages and other uses of the present apparatus will become more apparent by referring to the following detailed description and drawing in which.

DETAILED DESCRIPTION

Hereinafter, a description will be made to embodiments of the present invention with reference to the accompanying drawings.

Figure 1:
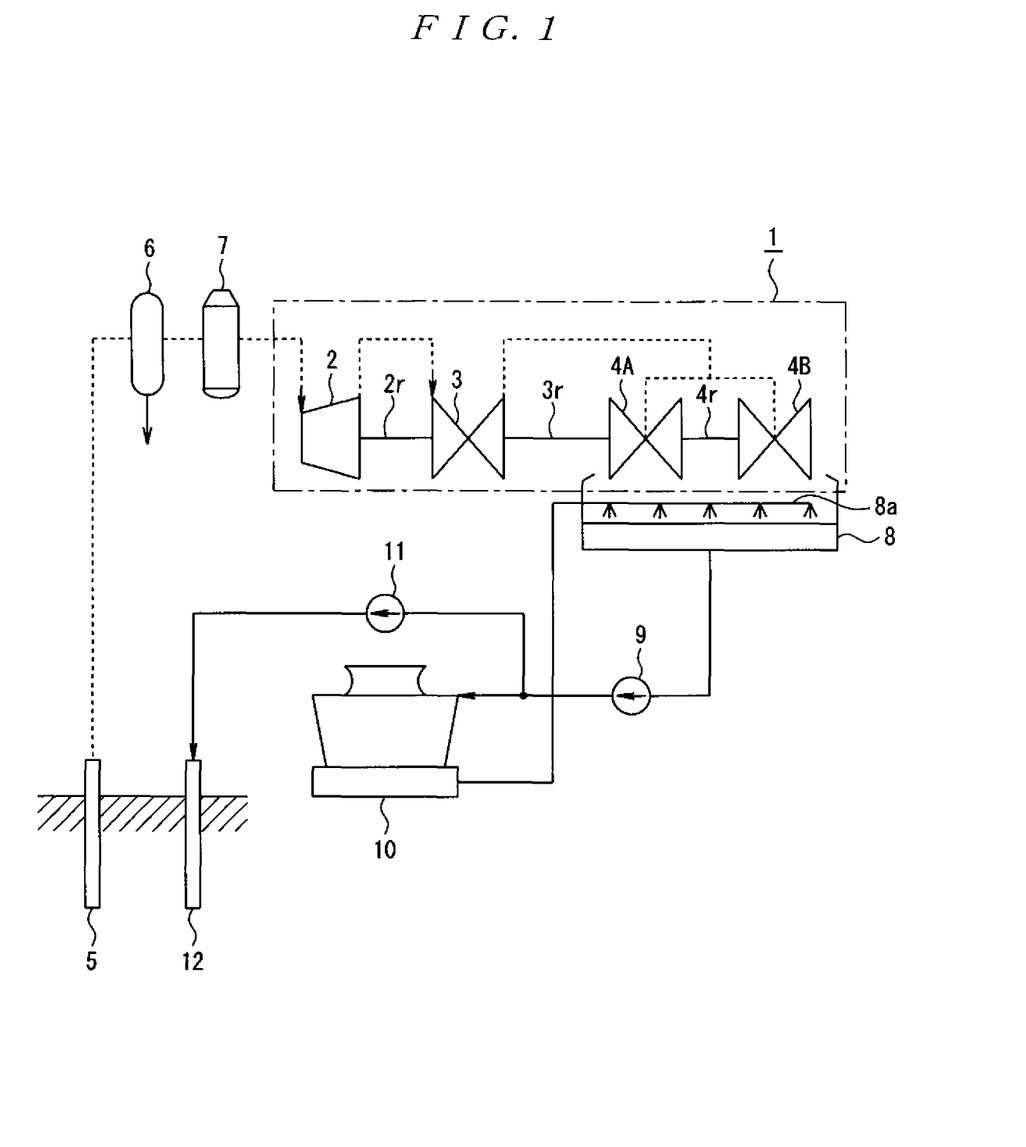
FIG. 1 is a schematic diagram showing a schematic construction of a steam turbine to which the present invention may be applied.

FIG. 1 is a schematic diagram showing a schematic configuration of a steam turbine to which the present invention may be applied. In FIG. 1, a reference numeral 1 denotes a steam turbine, which comprises a high-pressure turbine 2, a middle-pressure turbine 3, and two low-pressure turbines 4A and 4B. Among those, the geothermal steam supplied e.g. from a geothermal fluid production well 5 of a geothermal power plant is separated by a high-pressure separator 6 into steam and hot water. The separated steam is washed and supplied to the high-pressure turbine 2 through a scrubber 7 to remove mist. With the steam supplied to the high-pressure turbine 2, a turbine rotor $2r$ is rotated. The steam of which kinetic energy for rotating the turbine rotor $2r$ is released in the high-pressure turbine 2 is then supplied to the middle-pressure turbine 3 where a turbine-rotor $3r$ is rotated. The steam of which kinetic energy for rotating the turbine rotor $3r$ is released in the middle-pressure turbine 3 is finally supplied to the low-pressure turbines 4A and 4B where a turbine rotor $4r$ is rotated.

Then, the steam of which most of kinetic energy is exhausted that is emitted from the low-pressure turbines 4A and 4B is condensed by a steam condenser 8 for condensation and the condensed water is heated by a hot well pump 9. The greater part of the heated condensed water is in turn supplied to a cooling tower 10 for cooling, and the residual is reheated by a condensed water re-injection pump 11. The reheated condensed water is supplied to an injection well 12 to ultimately return back to the underground.

Cold water cooled in the cooling tower 10 is returned buck to a water sprinkle header $8a$ of the steam condenser 8.

Figure 2:
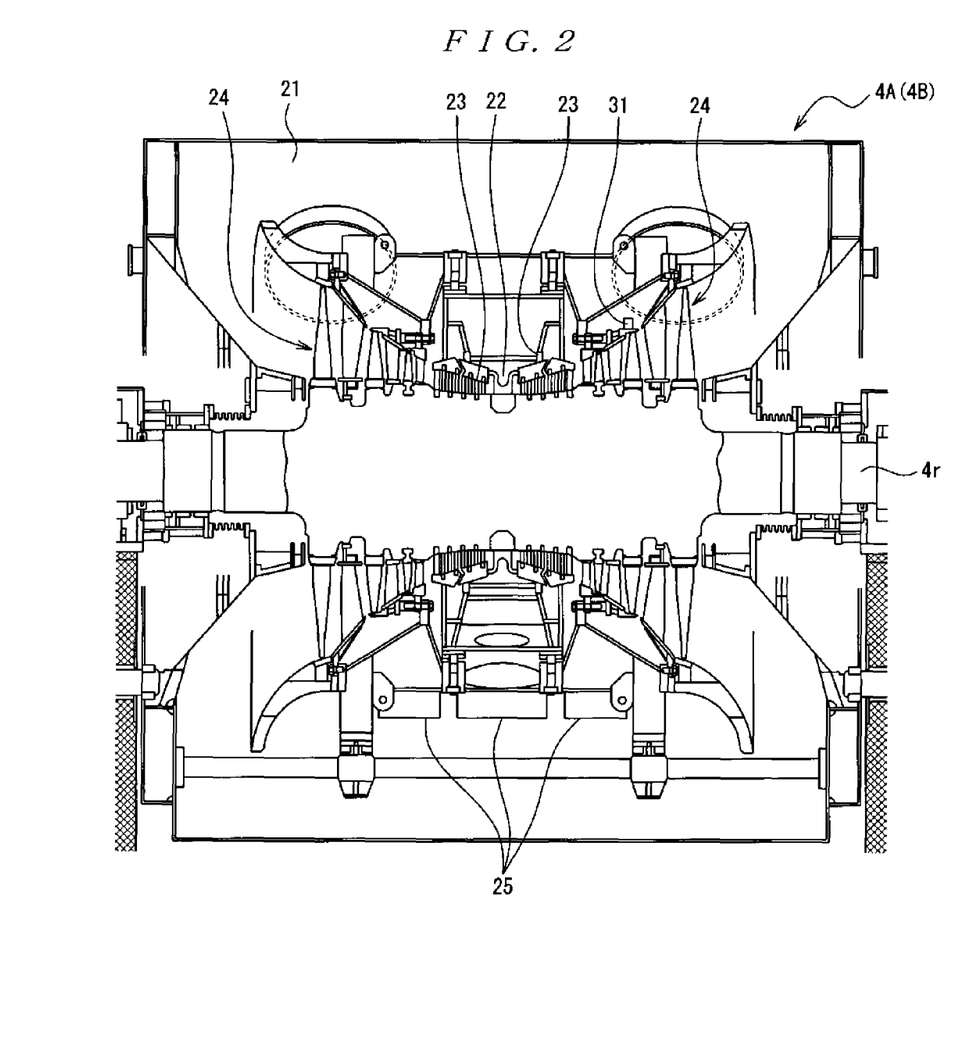
FIG. 2 is a cross-sectional view showing a low-pressure turbine.

Hereupon, each of the low-pressure turbines 4A and 4B, as shown in FIG. 2, is provided with casing 21 and a turbine rotor $4r$ rotatably arranged within the casing 21. The casing has a steam inlet 22 formed at its center to which steam supplied from the middle-pressure turbine 3 flows. At a position opposed to the steam inlet 22 of the turbine rotor $4r$, a pair of reaction blades 23 is provided. Further, at the outside of the reaction blades 23 of the turbine rotor $4r$, a low-pressure blade cascade 24 is respectively provided as a turbine blade cascade, and at a shaft end of the low-pressure blade cascade 24, a steam outlet 25 is formed.

Figure 3:
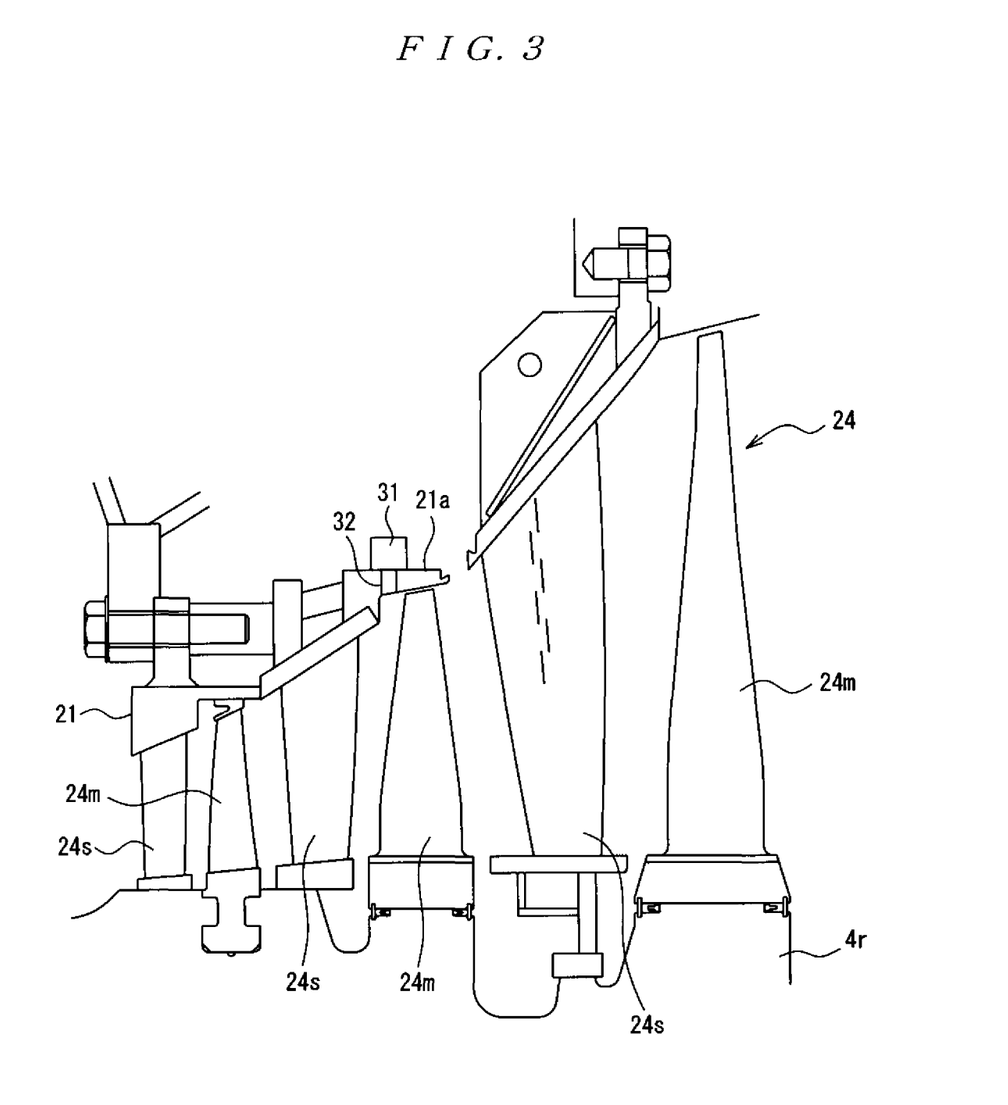
FIG. 3 is an enlarged view showing a mounting section of a corrosion factor monitoring system of a low-pressure turbine.

The low-pressure blade cascade 24, as shown in large size in FIG. 3, is alternately provided with a moving blade $24m$ mounted on the turbine rotor $4r$ and a static blade $24s$ mounted on the casing 21. The length of the moving blade $24m$ and of the static blade $24s$ in a radial direction is set such that the length gets longer as it goes toward outside from the center of the turbine rotor $4r$. Here, the turbine rotor $4r$ is made e.g. of 1% CrMoV steel and 12% Cr steel, etc., and the moving blade $24m$ is made e.g. of 13% Cr steel.

At an upper position at a rotor fitting section side in an inner peripheral surface of the casing 21 that is positioned close and opposite to a tip of the moving blade $24m$ at the center in an axial direction of the low-pressure blade cascade 24, a corrosion factor measuring device 31 of a corrosion factor monitoring device 30 is arranged.

Figure 4:
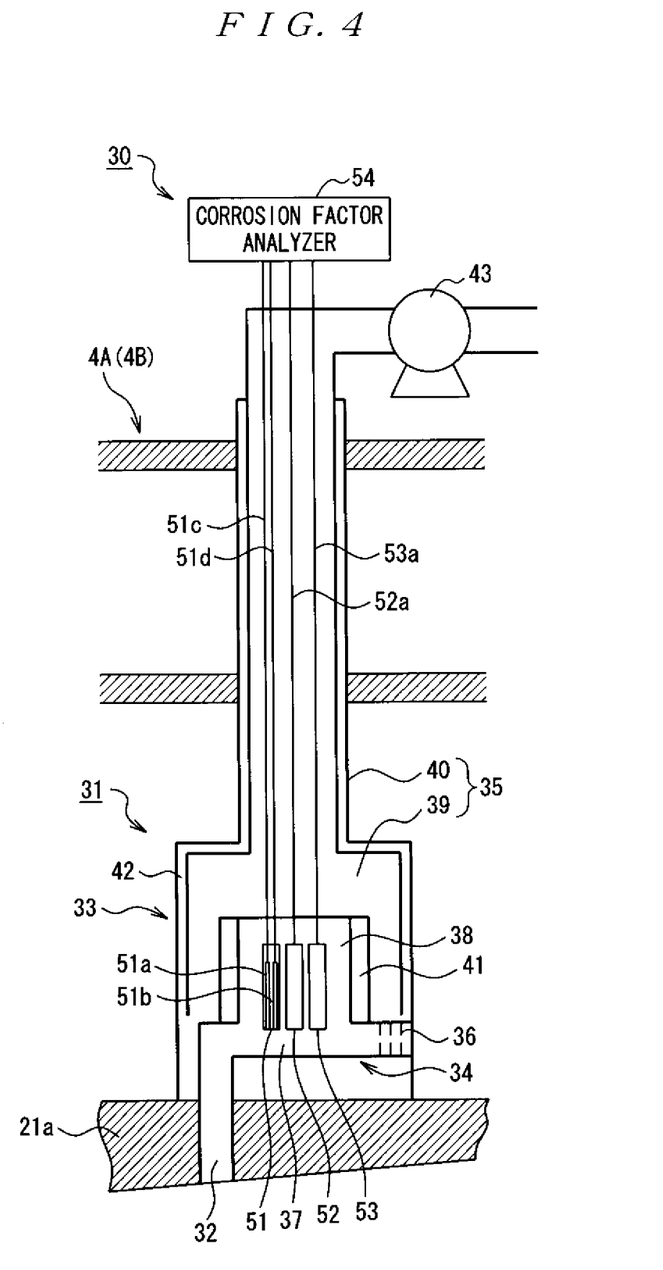
FIG. 4 is an enlarged view showing a first embodiment of the corrosion factor monitoring system.

As shown in FIGS. 3 and 4, the corrosion factor measuring device 31 has a communication hole 32 open to an inner peripheral surface of the casing 21 drilled at a position shifted to the inside in an axial direction from the tip of the moving blade $24m$ which is provided in an inner wall $21a$ of the casing 21. Further, the corrosion factor measuring device 31, as shown in FIG. 4, has a condensing mechanism 33 which communicates with an inner end of the communication hole 32. The condensing mechanism 33 has a condensation chamber 34 communicating with the communication hole 32 and a temperature control section 35 surrounding the condensation chamber 34.

The condensation chamber 34 comprises a condensed water storage 37, one end of which communicates with the communication hole 32 and the other end of which communicates with a low-pressure side of the inside of the casing 21 via a single-stage or a multi-stage orifice 36 to extend in an axial direction of the turbine rotor 4r; and a condensing section 38 upwardly extending from a middle part of the condensed water storage 37. Herein, the condensed water storage 37 is configured to have a structure for imitating a clearance gap of corrosive-prone parts at an inner peripheral side of the casing 21. An example of the structure imitating the clearance gap includes a fitting clearance formed between the moving blade 24m and the turbine rotor 4r, and a clearance gap formed between the tip of the moving blade 24m and the casing inner wall 21a of the casing 21, etc.

The temperature control section 35 comprises a cooling section 39 surrounding the condensing section 38, and a communicating section 40 communicating with the cooling section 39 to further communicate with the outside of the casing 21. In the cooling section 39, a Peltier element 41 is arranged, as a cooling member, at the outside of a peripheral wall of the condensing section 38. The cooling section 39 and the communicating section 40 have at an outer peripheral side an air passageway 42 to supply cooled air from the outside of the casing 21 to the cooling section 39, the inside of which is communicated with an air inlet of a heat radiating fan 43. This emits toward the outside air within the cooling section 39 by activating the heat radiating fan 43, which is heated by a heating section at the outer peripheral side of the Peltier element 41.

Then, a tip of a corrosion potential sensor 51, a pH sensor 52, and a chloride ion sensor 53 as a corrosion factor sensor is immersed into the condensed water stored in the condensed water storage 37. The corrosion potential sensor 51 has a sample member electrode 51a made of the same material (13% Cr steel) as that of the moving blade 24m serving as a structural member, and a reference electrode 51b. Lead wires 51c,51d,52a, and 53a pulled out from the corrosion potential sensor 51, the pH sensor 52, and the chloride ion sensor 53 are extended to the outside of the casing 21, through the inside of the cooling section 39 and the communicating section 40, and are connected to the corrosion factor analyzer 54.

In the corrosion factor analyzer 54, evaluation and judgment processing of the corrosion factors is performed based on corrosion potential, pH, and chloride ion concentration detected by the corrosion potential sensor 51, the pH sensor 52, and the chloride ion sensor 53.

(a) An account is given of plural corrosion factors (corrosion potential, pH, and chloride ion concentration) of the steam turbine.

The chloride ion concentration is a main corrosion factor of the steam turbine, which brings about formation of chloride, generation of hydrogen ions by hydrolysis of the chloride, and a rise in hydrogen ion concentration. That is, in the event of occurrence of corrosion pitting caused by chloride ions, it tends to rise in the chloride ion concentration in the corrosion pitting.

pH is representative of the hydrogen ion concentration in solution. The raise in the hydrogen ion concentration (i.e., pH decrease) accelerates ionization (i.e., oxidation reaction) of a member.

The corrosion potential is indicative of corrosivity versus the solution to which each member is touched. The higher the potential is, the larger the corrosion-prone is. The higher the hydrogen ion concentration is, the higher the corrosion potential is.

(b) As for a specific corrosion factor, the geothermal steam turbine includes carbonic dioxide gas and hydrogen sulfide.

The carbonic dioxide gas changes into carbonic acid in the condensed water where hydrogen ions are generated.

The hydrogen sulfide constitutes iron sulfide that plays a role of protection of a surface of the member, but may decompose by an action of chloride ion, causing pitting corrosion.

As stated in the above, the corrosion potential is affected by chloride ion concentration and pH, and therefore it could be a parameter representing to what extent corrosion is progressed in the member. What is important from a prevention maintenance standpoint is to know a primary factor of corrosion potential fluctuations. Measuring basic factors such as the pH and the chloride ion concentration provides more accurate understanding and prospection of corrosion conditions, and improves the accuracy of for what attention should be paid in steam environment, which helps precise determination as to which countermeasures have to be taken to operation and maintenance.

Hereupon, the measures to operation and maintenance include setting of a replacement cycle of the moving blade 24m and injection control of corrosion protection chemicals, etc.

As evaluation and judgment processing of the corrosion factors, the processing involves measuring by means of a potentiometer corrosion potential by measuring potential of the sample member electrode 51a and potential of the reference electrode 51b detected by the corrosion potential sensor 51; comparing fluctuations of the measured corrosion potential with fluctuations of simultaneously measured pH and chloride ion concentration; determining whether fluctuation factors of the corrosion potential are due to a decrease in a pH and a rise in the chloride ion concentration; and conducting injection control of corrosion protection chemicals efficacious to suppress the pH decrease and the rise in the chloride ion concentration depending on the determined results.

The corrosion factor analyzer 54 is provided with the residual life diagnostic equipment for predicting the life of the moving blade 24m using e.g. the corrosion potential and damage degradation characteristic data for the moving blade 24m. Herein, the damage degradation characteristic data which is data obtained e.g. by experimentally finding in advance a correlation between a damage degradation rate indicative of influence on corrosion damage to the moving blade 24m and the corrosion potential for representing the correlation as a characteristic map or a prediction model formula. The characteristic map or the prediction model formula is previously stored in a storage device. By referring to the characteristic map based on the measured corrosion potential, or by substituting the measured corrosion potential for the prediction model formula, a prediction is made about to what extent the damage degradation is progressed in the moving blade 24m, thus predicting the residual life of the moving blade 24m. Subsequently, based on the predicted residual life of the moving blade 24m, a replacement period of the moving blade 24m is set.

Moreover, the corrosion potential analyzer 54 has a corrosion environment state determining device installed therein for comparing the corrosion factor measured data, such as corrosion potential, pH, and chloride ion concentration, etc., measured by the corrosion factor measuring device 31 with a range of control criterion of a corresponding corrosion factor, and for raising an alarm when the corrosion factor measured data goes beyond the range of control criterion.

An explanation will next be made to an operation of the above-mentioned embodiment.

As shown in FIG. 1, geothermal steam belched out from the geothermal fluid production well 5 is separated by the high-pressure separator 6 into steam and hot water, and the separated steam is supplied to the scrubber 7 where the steam is washed to remove mist, and thereafter flows to the high-pressure turbine 2 of the steam turbine 1. The steam causes the turbine rotor 2r of the high-pressure turbine 2 to rotate where kinetic energy of the steam is released to rotate the turbine rotor 2r, then is supplied to the middle-pressure turbine 3 to rotate the turbine rotor 3r, and finally is supplied to the low-pressure turbines 4A and 4B to rotate the turbine rotor 4r. The steam of which most of energy is exhausted that is emitted from the low-pressure turbines 4A and 4B is condensed by the steam condenser 8 for condensation and the condensed water is heated by the hot-well pump 9. The greater part of the heated condensed water is supplied to the cooling tower 10 for cooling, and the residual is reheated by the condensed water re-injection pump 11 to supply to the injection well 12. The reheated residual is ultimately returned back to the underground.

Steam temperature of the steam turbine 1 in operation reaches 500 to 600° C. or so at a high temperature section, and rises to 100 to 200° C. at a low pressure section as well. The reason why the corrosion factors occur and progress are primarily due to condensation of steam, a change into aqueous solution, production of water, occurrence of an electrochemical corrosion reaction of the member, and progress of the corrosion reaction.

There is some possibility that the condensed water could occur incidental to temperature reduction within the turbine in suspension, or in fitting clearance between the moving blade 24m and the turbine rotors 2r to 4r in operation. The condensed water is more likely to occur in the low-pressure section at which temperature in the turbine is relatively low.

Therefore, with measurement of the corrosion factors at the low-pressure turbines 4A and 4B, it enables understanding of corrosion environment conditions.

In the present embodiment, as shown in FIGS. 3 and 4, the corrosion factor measuring device 31 of the corrosion factor monitoring device 30 is arranged, which communicates with an inner peripheral surface opposing, at slight intervals, a tip of the moving blade 24m of the turbine rotor 4r of the casing 21 of the low-pressure turbines 4A and 4B, for allowing introduction of steam thereinto.

In the corrosion factor measuring device 31, steam is introduced through a communication hole 32 formed in an inner peripheral wall of the casing 21 into the condensation chamber 34. More particularly, the steam introduced through the communication hole 32 enters a condensing section 38 provided upward thereof via the condensed water storage 37 at its low pressure side end of which an orifice 36 is provided. In the condensing section 38, a Peltier element 41 is arranged therearound. Thus, supplying a direct current to the Peltier element 41 exhibits its cooling effect, and cools the inside of the condensing section 38. This condenses steam into condensed water, and then is stored in the condensed water storage 37. At that moment, the heating section at the outer periphery side of the Peltier element 41 generates heat, but heated air in the temperature control section 35 is suctioned by the heat radiating fan 43 to the outside of the casing 21 by actuating the cooling fan 43. In keeping with this, cooling air standing outside of the casing 21 is introduced through an air passageway 42 into the cooling section 39.

Since in the condensed water storage 37, the tip of the corrosion potential sensor 51, the pH sensor 52, and the chloride ion sensor 53 as a corrosion factor sensor is immersed into the condensed water, it allows detection of corrosion potential, pH, and chloride ion concentration, during operation of the low-pressure turbines 4A and 4B, by means of the corrosion potential sensors 51, the pH sensor 52, and the corrosion potential sensor 53. These sensors 51, 52, and 53 are coupled to the corrosion factor analyzer 54 arranged outside of the casing 21 through the cooling section 39 and the communicating section 40 of the temperature control section 35.

On this account, in the corrosion factor analyzer 54, a potential difference between the sample member electrode 51a and the reference electrode 51b of the corrosion potential sensor 51 is measured by the potentiometer for measuring corrosion potential. The measured corrosion potential is stored in a corrosion factor memory area in the storage device, and an input pH value and a chloride ion concentration value are also stored simultaneously in the corrosion factor memory area.

In this way, since the corrosion potential, the pH, and the chloride ion concentration are stored, at predetermined time intervals, in the corrosion factor memory area, comparing the present corrosion potential, the pH, and the chloride ion concentration with the past corrosion potential, the pH, and the chloride ion concentration stored in the corrosion factor memory area allows correct understanding of fluctuations of the corrosion potential, the pH, and the chloride ion concentration.

At this time, the comparison of fluctuations of the corrosion potential with the fluctuations of the pH and the chloride ion concentration enables discrimination of whether fluctuation factors of the corrosion potential are due to a rise in hydrogen ion concentration caused by pH a decrease, due to a rise in hydrogen ion concentration caused by a rise in the chloride ion concentration, or due to the both of the pH decrease and the rise in the chloride ion concentration. For this reason, if the fluctuation factors are due to the pH decease, injection of corrosion protection chemicals, efficacious to increase pH, into a steam system of the steam turbine 1 is controlled to suppress the rise in hydrogen ion concentration. Otherwise, if the fluctuation factors of the corrosion potential are due to the rise in the chloride ion concentration, injection of corrosion protection chemicals, efficacious to suppress the rise in the chloride ion concentration, into the steam system of the steam turbine 1 is controlled for carrying out corrosion protection processing.

By referring to a characteristic map of the damage degradation characteristic data stored in the storage device based on the measured corrosion potential, or by substituting the measured corrosion potential for a prediction model formula, the residual life of the moving blade 24m is predicted and a replacement period of the moving blade 24m is set based on the predicted residual life of the moving blade 24m.

In this manner, according to the above-mentioned embodiment, the condensing mechanism 33 is provided within the casing 21 of the low-pressure turbines 4A and 4B of the steam turbine 1 to introduce steam standing between the moving blade 24m and a casing inner wall 21a for condensation. Therefore, it is allowed to produce condensed water by condensing steam by means of the condensing mechanism 33 during operation of the low-pressure turbines 4A and 4B; detect the corrosion potential, the pH, and the chloride ion concentration, as corrosion factors, contained in the produced condensed water by means of the corrosion potential sensor 51, the pH sensor 52, and the chloride ion sensor 53, respectively; and supply a detection signal to the corrosion factor analyzer 54. Thus, it enables at all times correct measurement of the corrosion factors contained in the steam in the low-pressure turbines 4A and 4B in operation. Consequently, it makes it possible to take an exact measure of operation and maintenance such as prediction of the residual life of the moving blade 24m, and injection control of the corrosion prevention chemicals by the corrosion factor analyzer 54 based on the measured corrosion factors.

What is more, since it is configured to energize the Peltier element 41 to the condensing section 38 in the condensing mechanism 33 to cool steam for condensation, downsizing of the arrangement of the condensing mechanism 33 can be achieved. Moreover, since the orifice 36 is provided at the low-pressure side of the condensed water storage 37 in the condensing mechanism 33, it prevents a direct outflow of steam having relatively high pressure supplied from the communication hole 32 to the low-pressure side in the casing 21. This keeps pressure in the condensed water storage 37 at a relatively high level, thereby exerting no influence on the steam within the casing inner wall 21a of the casing 21.

While in the aforesaid embodiment, a description was made giving an example where the heat radiating fan 43 is provided to introduce cooling air into the temperature control section 35, the invention is not limited thereto. A blower fan may of course be communicated with the air passageway 42 in place of the heat radiating fan 43.

Further, in the aforesaid embodiment, while a description was made, giving an example where the corrosion factor analyzer 54 is provided in both of the low-pressure turbines 4A and 4B to analyze corrosion factors of the low-pressure turbines 4A and 4B in operation, the invention is not limited thereto. It may of course analyze the corrosion factors of the low-pressure turbines 4A and 4B by one corrosion factor analyzer 54. Furthermore, a description was made, giving an example, where the damage and degradation life of the moving blade 24m is predicted based on a measured value of the corrosion factors in operation by the corrosion factor analyzer 54. In this occasion, it may sample the condensed water produced with temperature reduction of steam in the casing 21 when the low-pressure turbines 4A and 4B are stopped, detect corrosion factors of the sampled condensed water by means of the corrosion potential sensor, the pH sensor, and the chloride ion sensor, and supply the corrosion factors to the corrosion factor analyzer 54. Subsequently, a correlation between a corrosion factor measured value in operation and a corrosion factor measured value of the condensed water sampled from an actual machine in suspension is found to take it as a management factor, which strives for accuracy improvement of the measured value of the corrosion factors.

In this case, as a candidate of condensed water sampling parts by the actual machine, it would be preferable to select corrosion-prone parts, including a fitting clearance gap formed between the moving blade 24m and the turbine rotor 4r, a surface of the moving blade 24m, and a surface of the turbine rotor 4r, etc.

Further, while in the aforesaid embodiment a description was made giving an example where the corrosion factor analyzer 54 is installed outside of the casing 21, the invention is not limited thereto. The invention may of course install the corrosion factor analyzer 54 inside of the casing 21, on condition that one takes measures so as not to be subject to influence of temperature and humidity.

Moreover, since in the aforesaid embodiment the condensed water storage 37 is provided in the condensing mechanism 33 with any condensed water sampling mechanism provided to take out, outside of the casing 21, the condensed water stored in the condensed water storage 37, it allows sampling of the condensed water in operation. Besides, with the corrosion factors of the sampled condensed water detected by the corrosion factor sensor, it becomes possible to determine aging degradation of the corrosion potential sensor 51, the pH sensor 52, and the chloride ion sensor 53 of the corrosion factor measuring device 31, thereby correcting detected values from each sensor 51 to 53.

An explanation will next be made to a second embodiment of the present invention in terms of FIG. 5.

The second embodiment is excogitated for ease of replacement of the corrosion factor sensor.

Figure 5:
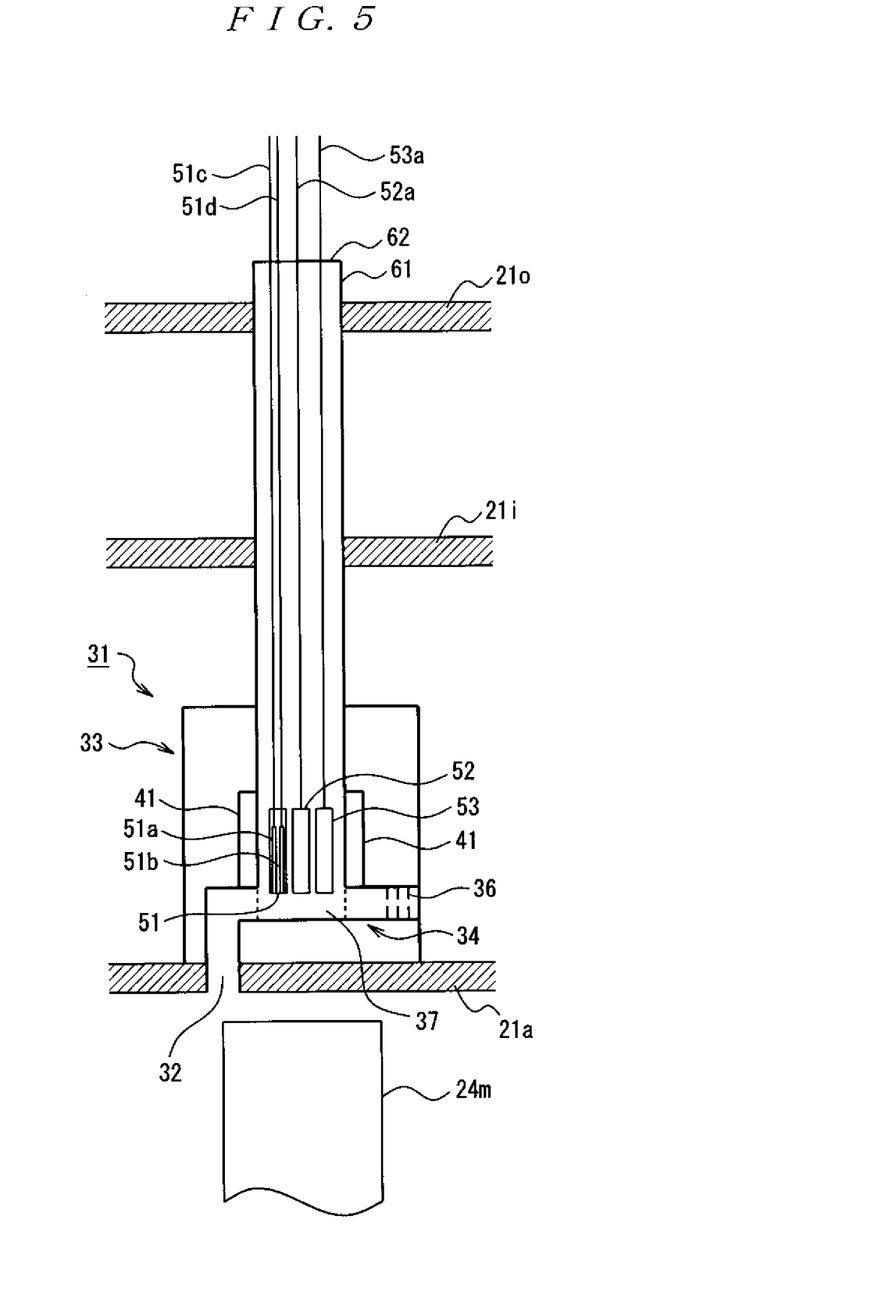
FIG. 5 is an enlarged view showing a second embodiment of the corrosion factor monitoring system.

Namely, in the second embodiment, as shown in FIG. 5, it is configured to arrange a conduit 61 in the casing 21 of the low-pressure turbines 4A and 4B, which extends from an outermost periphery outer casing 210 to the condensed water storage 37 of the condensing mechanism 33 passing through the inner casing 21i; insert the corrosion potential sensor 51, the pH sensor 52, and the chloride ion sensor 53, as a corrosion sensor, into the conduit 61 to immerse a lower end of these sensors 51 to 53 into the condensed water stored in the condensed water storage 37. An end projecting from the outer casing 210 of the conduit 61 is sealed by a detachable sealing lid 62 for holding lead wires 51c,51d of the corrosion potential sensor 51, a lead wire 52a of the pH sensor 52, and a lead wire 53a of the chloride ion sensor 53, with inserting these lead wires thereinto. The conduit 61 is movably attached between a condensed water blocking position at which a lower surface of the conduit 61 contacts the base of the condensed water storage 37 and a condensed water passing position at which the passing position is substantially flush with an upper surface of the condensed water storage 37.

According to the second embodiment, when replacing one or plural sensors consisting of the corrosion potential sensor 51, the pH sensor 52, and the chloride ion sensor 53, the lower surface of the conduit 61 first contacts the base of the condensed water storage 37 to thereby block intrusion of high-pressure steam within the casing inner wall 21a. In this state, the sealing lid 62 is detached from an upper end of the conduit 61 to open the upper end of the conduit 61, and a lead wire of the sensor to be replaced is pulled out. Thereby, the sensor to be replaced is taken out outside of the outer casing 210 from the conduct 61 and the lead wire is also removed from the sealing lid 62.

Then, a new lead wire of the sensor is inserted into the sealing lid 62, a sensor is inserted into the conduit 61 under conditions where the sensor is adjusted to the length enough for the sensor to immerse into the condensed water, and the sealing lid 62 is attached on the upper end of the conduit 61. Next, the conduit 61 is raised such that its lower surface is substantially flush with the upper surface of the condensed water storage 37, and condensed water is poured into the conduit 61, so that the lower surface of the corrosion potential sensor 51, the pH sensor 52, and the chloride ion sensor 53 is immersed into the condensed water.

In this way, constructing the conduit 61 in a movable fashion between the condensed water blocking position and the condensed water passing position blocks outflow of steam inside of the casing inner wall 21a to the outside of the casing 21, through the conduit 61, even when the low-pressure turbines 4A and 4B are in operation. This ensures easy and safe once or multiple times replacements of the corrosion potential sensor 51, the pH sensor 52, and the chloride ion sensor 53 serving as a corrosion factor sensor.

It is to be noted that while in the first and the second embodiments, a description was made giving an example, where the three sensors consisting of the corrosion potential sensor 51, the pH sensor 52, and the chloride ion sensor 53 are applied as a corrosion factor sensor, the invention is not limited thereto. For example, only the corrosion potential sensor 51 may be provided, or an electric conductivity sensor may be added to detect electric conductivity of the condensed water, to simultaneously measure electric conductivity of the condensed water in order to aim at accuracy improvement of the corrosion factor analysis. In addition, where steam contains carbonic dioxide gas and hydrogen sulfide as in the case of steam of a geothermal plant facility, a carbonic dioxide gas sensor and a hydrogen sulfide sensor may also be added, as a corrosion factor sensor, for the purpose of further improving accuracy of corrosion factor analysis.

Further, whereas in the first and the second embodiments a description was made giving an example where the steam turbine 1 is applied to the geothermal plant facility, the invention is not limited thereto. The steam turbine 1 may be applied to a thermal power station facility and another any facilities.

Furthermore, while in the first and the second embodiments a description was made giving an example where the steam turbine 1 is provided with two low-pressure turbines 4A and 4B, the invention is not limited thereto. The present invention may be applied to an instance where only one low-pressure turbine is provided.

Moreover, while in the first and the second embodiments a description was made giving an example where the Peltier element is applied as a cooling member of the condensing mechanism 33, the invention is not limited thereto. Another cooling device may be applied.

According to the present invention, the corrosion environment monitoring system and the corrosion environment monitoring method capable of measuring corrosion factors within the steam turbine for ensuring accurate corrosion environment monitoring is provided.

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. A corrosive environment monitoring system for measuring a corrosion factor, the monitoring system comprising:
   a corrosion factor measuring device in contact with an inside of a steam turbine, the corrosion factor measuring device including:
   a condensing chamber for condensing steam flowed into the condensing chamber, which allows for influx of steam within the steam turbine thereinto;
   a condensed water storage unit housed within the condensing chamber, the condensed water storage unit configured to store the condensed water produced by condensing the steam; and
   a corrosion factor sensor within the condensing chamber, the corrosion factor sensor measuring the corrosion factor of the condensed water within the condensed water storage unit.

2. The corrosion environment monitoring system according to claim 1 further comprising a temperature control section surrounding the condensing chamber, the temperature control section configured to cool the steam flowed into the condensing chamber.

3. The corrosion environment monitoring system according to claim 1, wherein the corrosion factor measuring device comprises at least three types of sensors including a corrosion potential sensor, a pH sensor, and a chloride ion sensor.

4. The corrosion environment monitoring system according to claim 3, wherein the corrosion potential sensor includes a sample member electrode made of the same material as the structural member and a reference electrode, the sample member electrode and the reference electrode being immersed into condensed water stored in the condensed water storage unit.

5. The corrosion environment monitoring system according to claim 3, wherein the corrosion factor measuring device includes an electric conductivity sensor as one of the at least three types of sensors.

6. The corrosion environment monitoring system according to claim 1, wherein the steam turbine comprises a high-pressure turbine, a middle-pressure turbine, and a low-pressure turbine, and
   the corrosion factor measuring device is arranged at a position where a part of steam flux flowing inside of a turbine blade cascade can be sampled, without affecting the steam flux inside of the turbine blade cascade, in a casing of the low-pressure turbine.

7. The corrosion environment monitoring system according to claim 1, further comprising a corrosion factor analyzer including a corrosive environment state factor determining device that compares corrosion factor measured data measured by the corrosion factor measuring device and a control reference range of a corresponding corrosion factor, and that raises an alarm when the corrosion factor measured data goes beyond the control reference range.

8. The corrosion environment monitoring system according to claim 1, further comprising a corrosion factor analyzer including a residual life diagnosis device that predicts the progress of corrosion damage to the structural member based on a previously prepared correlation and the corrosion factor measured data measured by the corrosion factor measuring device to find the residual life of the structural member.

9. A corrosion environment monitoring method of measuring a corrosion factor participating in damage degradation of a structural member inside of a steam turbine, comprising:
   producing condensed water by flowing steam standing in the steam turbine into a condensing chamber within the steam turbine when the steam turbine is in operation;
   measuring a corrosion factor during operation of the steam turbine by contacting a corrosion factor sensor within the condensing chamber with the condensed water;
   analyzing the corrosion factor by gathering the condensed water in a structural member inside of the steam turbine when the steam turbine is not in operation;
   comparing corrosion factor data measured when the steam turbine is in operation with corrosion factor data analyzed when the steam turbine is not in operation; and
   finding a correlation between the corrosion factor data measured when the steam turbine is in operation and the corrosion factor data analyzed when the steam turbine is not in operation to adopt the correlation as a management indicator.

10. The corrosion environment monitoring system according to claim 1, further comprising a corrosion factor analyzer that receives measured corrosion factor data from the condensed water gathered when the steam turbine is not in operation that finds a correlation between a corrosion factor value measured when the steam turbine is in operation and a corrosion factor value measured when the steam turbine is not in operation, and that adopts the correlation as a management indicator.

11. The corrosion environment monitoring system according to claim 1, wherein the condensed water storage unit has an orifice provided at a low pressure side.

12. The corrosion environment monitoring system according to claim 1, wherein the condensed water storage has one end communicating with a communication hole formed on an inner peripheral wall of a casing, and has another end communicating with a low pressure side inside of the casing through an orifice.

13. The corrosion environment monitoring system according to claim 1 wherein a conduit is provided in the steam turbine, which extends from an outer casing at an outermost periphery up to the condensed water storage unit passing through an inner casing, the corrosion factor sensor is inserted into the conduit to dip a lower end of the corrosion factor sensor into the condensed water stored in the condensed water storage unit, and the conduit is movably mounted between a condensed water blocking position where an underside of the conduit comes into contact with a base of the condensed water storage unit and a condensed water passing position where the underside of the conduit is flush with an upper surface of the condensed water storage unit.

14. The corrosion environment monitoring system according to claim 10, wherein the condensed water storage unit has an orifice provided at a low pressure side.

15. The corrosion environment monitoring system according to claim 10, wherein the condensed water storage unit has one end communicating with a communication hole formed on an inner peripheral wall of a casing, and has another end communicating with a low pressure side inside of the casing through an orifice.

16. The corrosion environment monitoring system according to claim 10, wherein a conduit is provided in the steam turbine, which extends from an outer casing at an outermost periphery up to the condensed water storage unit passing through an inner casing, the corrosion factor sensor is inserted into the conduit to dip a lower end of the corrosion factor sensor into the condensed water stored in the condensed water storage, and the conduit is movably mounted between a condensed water blocking position where an underside of the conduit comes into contact with a base of the condensed water storage unit and a condensed water passing position where the underside of the conduit is flush with an upper surface of the condensed water storage unit.

* * * * *